(12) United States Patent
Park et al.

(10) Patent No.: US 9,161,933 B2
(45) Date of Patent: Oct. 20, 2015

(54) SOLID PHARMACEUTICAL COMPOSITION COMPRISING AMLODIPINE AND LOSARTAN AND PROCESS FOR PRODUCING SAME

(75) Inventors: Jae Hyun Park, Suwon-si (KR); Kyeong Soo Kim, Suwon-si (KR); Ho Taek Yim, Yongin-si (KR)

(73) Assignee: HANMI SCIENCE CO., LTD, Hwaseong-si (KR)

( * ) Notice: Subject to any disclaimer, the term of this patent is extended or adjusted under 35 U.S.C. 154(b) by 0 days.

(21) Appl. No.: 13/139,673

(22) PCT Filed: Feb. 13, 2009

(86) PCT No.: PCT/KR2009/000704
§ 371 (c)(1),
(2), (4) Date: Jun. 14, 2011

(87) PCT Pub. No.: WO2010/085014
PCT Pub. Date: Jul. 29, 2010

(65) Prior Publication Data
US 2011/0245302 A1  Oct. 6, 2011

(30) Foreign Application Priority Data

Jan. 23, 2009  (KR) .................. 10-2009-0005840

(51) Int. Cl.
| | |
|---|---|
| A61K 31/4422 | (2006.01) |
| A61P 9/00 | (2006.01) |
| A61P 9/10 | (2006.01) |
| A61P 9/12 | (2006.01) |
| A61P 9/04 | (2006.01) |
| B29B 9/16 | (2006.01) |
| A61K 31/41 | (2006.01) |
| A61K 9/20 | (2006.01) |
| A61K 31/4178 | (2006.01) |
| A61K 31/44 | (2006.01) |

(52) U.S. Cl.
CPC .............. *A61K 31/41* (2013.01); *A61K 9/2013* (2013.01); *A61K 9/2027* (2013.01); *A61K 9/2054* (2013.01); *A61K 9/2059* (2013.01); *A61K 9/2077* (2013.01); *A61K 31/4178* (2013.01); *A61K 31/44* (2013.01); *A61K 31/4422* (2013.01)

(58) Field of Classification Search
USPC .............................................. 514/356; 264/6
See application file for complete search history.

(56) References Cited

U.S. PATENT DOCUMENTS

| | | | |
|---|---|---|---|
| 6,677,356 B1 | 1/2004 | Sethi et al. | |
| 6,936,625 B2 * | 8/2005 | Moon et al. | ............ 514/356 |
| 2002/0068740 A1 | 6/2002 | Mylari | |
| 2002/0099046 A1 | 7/2002 | Scott | |
| 2002/0187188 A1 * | 12/2002 | Cherukuri | ................ 424/465 |
| 2003/0232081 A1 | 12/2003 | Doshi et al. | |
| 2005/0209288 A1 | 9/2005 | Grogan et al. | |
| 2006/0128763 A1 | 6/2006 | Moon | |
| 2006/0276523 A1 | 12/2006 | Almirante et al. | |
| 2008/0051438 A1 | 2/2008 | Nagahama et al. | |

FOREIGN PATENT DOCUMENTS

| | | |
|---|---|---|
| CA | 2672549 A1 | 6/2003 |
| CA | 2749903 A1 | 7/2010 |
| CA | 2749955 A1 | 7/2010 |
| EP | 1 314 425 A1 | 5/2003 |
| JP | 2008-543729 A | 12/2008 |
| KR | 10-2008-0018841 A | 2/2008 |
| KR | 10-2008-0052852 A | 6/2008 |
| WO | 03/035046 A2 | 5/2003 |
| WO | 03/097045 A1 | 11/2003 |
| WO | 2005/070463 A2 | 8/2005 |
| WO | 2006/048208 A1 | 5/2006 |
| WO | 2007/001065 A2 | 1/2007 |
| WO | 2007/056324 A2 | 5/2007 |
| WO | WO2007/049292 * | 5/2007 |
| WO | 2008010659 A1 | 1/2008 |
| WO | 2008/023958 A1 | 2/2008 |
| WO | 2008/044862 A1 | 4/2008 |
| WO | 2008/069612 A1 | 6/2008 |

OTHER PUBLICATIONS

Kohlmann et al (The "LOTHAR" Study: Evaluation of Efficacy and Tolerability of the Fixed Combination of Amlodipine and Losartan in the Treatment of Essential Hypertension, Arquivos Brasileros de Cardiologia, vol. 86, N 1, Jan. 2006, pp. 1-13).*
European Patent Office, European Office Action issued in corresponding EP Application No. 09838901.8, dated Jul. 9, 2012.
Japanese Patent Office, Japanese Office Action issued in corresponding JP Application No. 2011-547742, dated Oct. 8, 2013.
Joel M. Neutel, "Prescribing Patterns in Hypertension: The Emerging Role of Fixed-Dose Combinations for Attaining BP Goals in Hypertensive Patients," Current Medical Research and Opinions, 2008, vol. 24, No. 8, pp. 2389-2401.
Peruvian Patent Office, Peruvian Office Action issued in corresponding PE Application No. 000681-2009/DIN, dated Sep. 23, 2013.
Gokhale et al., "Efficacy and Safety of Losartan-Amplodipine Combination—An Indian Postmarketing Surveillance Experience," J Indian Med Assoc., 2002, vol. 100, No. 3, Abstract.
Colombian Patent Office, Colombian Office Action issued in corresponding CO. Application No. 11-105490, dated Jun. 20, 2013.
Egyptian Patent Office, Communication mailed Jul. 21, 2015, issued in corresponding Egyptian Application No. PCT 1216/2011.

* cited by examiner

*Primary Examiner* — Kathrien Cruz
(74) *Attorney, Agent, or Firm* — Sughrue Mion, PLLC (57) ABSTRACT

The present invention relates to a solid pharmaceutical composition for preventing or treating cardiovascular disorders comprising amlodipine or a pharmaceutically acceptable salt thereof and losartan or a pharmaceutically acceptable salt thereof, which exhibits high dissolution rates of amlodipine and losartan even under a low pH condition and improved storage stability.

5 Claims, 5 Drawing Sheets

SOLID PHARMACEUTICAL COMPOSITION COMPRISING AMLODIPINE AND LOSARTAN AND PROCESS FOR PRODUCING SAME

CROSS REFERENCE TO RELATED APPLICATIONS

This application is a National Stage of International Application No. PCT/KR2009/000704 filed Feb. 13, 2009, claiming priority based on Korean Patent Application No. 10-2009-0005840, filed Jan. 23, 2009, the contents of all of which are incorporated herein by reference in their entirety.

FIELD OF THE INVENTION

The present invention relates to a solid pharmaceutical composition for preventing or treating cardiovascular disorders comprising amlodipine or a pharmaceutically acceptable salt thereof and losartan or a pharmaceutically acceptable salt thereof, and a method for preparing the same.

BACKGROUND OF THE INVENTION

In the treatment of hypertension, it is more important to maintain the blood pressure within a normal range on a consistent basis than to simply lower the blood pressure level itself, for reducing the risks of complications such as coronary heart diseases and cardiovascular diseases, e.g., stroke, heart failure and myocardial infarction. Accordingly, antihypertensive agents should be effective for long-term treatment of hypertension. Further, advanced therapy using a combination of two or more drugs having different pharmacological actions makes it possible to improve preventive or therapeutic effects, while lowering side effects arising from the long term administration of a single drug.

Notable antihypertensive drugs include diuretics, sympatholytic agents and vasodilators. Vasodilators are most widely prescribed antihypertensive drugs, and they are divided into several groups according to their pharmacological action which include ACE (angiotensin converting enzyme) inhibitors, angiotensin II receptor antagonists and calcium channel blockers.

Amlodipine is the generic name for 3-ethyl-5-methyl-2-(2-aminoethoxy-methyl)-4-(2-chlorophenyl)-6-methyl-1,4-dihydro-3,5-pyridine dicarboxylate. Amlodipine besylate is currently marketed as Novasc (trade mark). Amlodipine is a long-acting calcium channel blocker which is useful in treating cardiovascular disorders such as agina, hypertension and congestive heart failure.

Losartan is the generic name for 2-butyl-4-chloro-1-[[2'-(1H-tetrazol-5-yl)[1,1'-biphenyl]-4-yl]methyl]-1H-imidazol-5-methanol, which has been disclosed in U.S. Pat. Nos. 5,608,075; 5,138,069; and 5,153,197. Losartan potassium is commercially available as Cozaar (trade mark). Losartan blocks the interaction of angiotensin II and its receptor, and is mainly used for treating hypertension, heart failure, ischemic peripheral circulatory disorder, myocardial ischemia (angina pectoris), diabetic neuropathy and glaucoma, and also for preventing the progression of post-myocardial infarction heart failure.

The present inventors have found that a combined formulation which comprises amlodipine and losartan having different pharmacological activities is useful for preventing or treating cardiovascular disorders, and have developed such an amlodipine-losartan combined composition having optimized physical and chemical properties.

SUMMARY OF THE INVENTION

Accordingly, it is an object of the present invention to provide a solid pharmaceutical composition containing amlodipine and losartan, which exhibits high dissolution rates of amlodipine and losartan even under a low pH condition and improved storage stability.

In accordance with one aspect of the present invention, there is provided a solid pharmaceutical composition for preventing or treating cardiovascular disorders comprising amlodipine or a pharmaceutically acceptable salt thereof and losartan or a pharmaceutically acceptable salt thereof. The inventive composition comprises amlodipine and losartan, preferably, in a form separated from each other, more preferably, in a granule form separated from each other. Further, controlling the amount of losartan leads to optimized dissolution rates of amlodipine and losartan in the inventive composition.

BRIEF DESCRIPTION OF THE DRAWINGS

The above and other objects and features of the present invention will become apparent from the following description of the invention, when taken in conjunction with the accompanying drawings which respectively show.

DETAILED DESCRIPTION OF THE INVENTION

The solid pharmaceutical composition of the present invention comprising amlodipine and losartan exhibits high dissolution rates of amlodipine and losartan even at a low pH, thereby achieving improved preventive or therapeutic effects for cardiovascular disorders, as compared with conventional single formulations, while minimizing adverse effects of the two drugs.

Amlodipine used in the present invention may be one of various forms of pharmaceutically acceptable salts. The pharmaceutically acceptable salts of amlodipine include hydrochloride, hydrobromide, sulphate, phosphate, acetate, maleate, fumarate, lactate, tartrate, citrate, gluconate, besylate and camsylate salts, but are not limited thereto. Among these salts, preferred are the amlodipine besylate and camsylate, and more preferred is the amlodipine camsylate. Also, amlodipine used in the present invention may be an amlodipine racemate and S-amlodipine.

Losartan used in the present invention may be one of various forms of pharmaceutically acceptable salts. The preferred pharmaceutically acceptable salt of losartan that can be used in the present invention is losartan potassium.

In the inventive composition, amlodipine or a pharmaceutically acceptable salt thereof and losartan or a pharmaceutically acceptable salt thereof may be used in amounts corresponding to a weight ratio in the range of 1:2.5 to 1:20, preferably 1:5 to 1:10.

The inventive composition can provide improved preventive or therapeutic effects for cardiovascular disorders such as angina pectoris, hypertension, artery vasospasm, deep vein, cardiac hypertrophy, cerebral infarct, congestive heart failure and myocardial infarction.

When the combined formulation of amlodipine and losartan is prepared by simply mixing the two drugs, gelation of losartan disadvantageously occurs. Losartan readily dissolves in purified water or is very well released at a relatively high pH (e.g., pH 6.8), but it is very slowly released at a low pH (e.g., pH 2.0 or pH 1.2) because of its gelation. In case of Cozaar (trade mark), a commercially available losartan preparation, the dissolution rate of losartan is below 30% thereof in 30 minutes at a pH range of 1.2 to 2.0. In the combined formulation of amlodipine and losartan, amlodipine may be locked in the inside of the formulation due to the gelation of losartan.

Further, the combined formulation prepared by simply mixing amlodipine and losartan has very poor storage stability mainly due to an undesired chemical reaction among amlodipine, losartan and excipients.

In order to overcome the above-mentioned problems such as losartan gelation and stability lowering, the combined formulation of amlodipine and losartan must be prepared by physically separating amlodipine from losartan.

As one embodiment to physically separate amlodipine from losartan to prepare the combined formulation, a two-layer tablet may be prepared by formulating separated granules of amlodipine into a tablet, mixing the tablet with a mixture comprising losartan, and formulating the resulting mixture into a two-layer tablet. However, this method has several problems in that it requires a specific two-layer tablet press machine, double mass deviation frequently occurs, and productivity becomes lowered due to decrease of a tableting speed. Accordingly, there exists a need for a study to develop a pharmaceutical composition which can be formulated by a general tablet press machine and a method for preparing same.

The present invention also includes within its scope a combined formulation of amlodipine and losartan in which the contact between the two drugs is minimized by physically separating amlodipine or a pharmaceutically acceptable salt thereof from losartan or a pharmaceutically acceptable salt thereof, and separately granulating them. Accordingly, preferably, the present invention provides a solid pharmaceutical composition comprising granule forms of amlodipine and losartan separated from each other.

In accordance with one embodiment of the present invention, the amlodipine-losartan combined formulation in which granule forms of amlodipine and losartan are separated from each other may be prepared by a method comprising the steps of (1) granulating amlodipine or a pharmaceutically acceptable salt thereof and losartan or a pharmaceutically acceptable salt thereof, respectively, to obtain respective separated granules; and (2) mixing the granules. The inventive combined formulation prepared by the above method does not suffer from lowering of stability for the reason that the mixing of amlodipine and losartan granules minimizes the contact dimension between the two drugs due to reduced specific surface areas of the granules and surrounding of respective drugs with used excipients. The combined formulations of Examples 1 to 7 prepared by this method exhibit an enhanced dissolution rate of amlodipine (see FIG. 1), and also exhibit high stability of amlodipine (see Table 2), as compared with the combined formulation of Comparative Example 1, which is a tablet obtained by simply mixing amlodipine and losartan.

The inventive composition may comprise pharmaceutically acceptable carriers or excipients in each of the amlodipine and losartan granules. The pharmaceutically acceptable carriers or excipients may include microcrystalline cellulose, lactose, mannitol, sodium citrate, calcium phosphate, glycine, starch, disintegrants (e.g., sodium starch glycolate, croscarmellose sodium, composite silicate and crosspovidone) and granulating binders (e.g., polyvinylpyrrolidone, hydroxypropylmethylcellulose (HPMC), hydroxypropylcellulose (HPC), sucrose, gelatine and acacia gum). Also, the inventive composition may further comprise lubricants such as magnesium stearate, stearic acid, glyceryl behenate and talc.

Nonetheless, the solid pharmaceutical composition comprising granule forms of amlodipine and losartan separated from each other still involves the risk that losartan becomes unsatisfactorily released under a low pH condition due to its gelation. It is expected that this problem significantly gives undesired effects on the bioavailability of the formulation because the formulation is first exposed to the acidic gastric juice having a low pH value when orally administered. Accordingly, considering that pH in the stomach of a normal adult is in a range of 1.0 to 3.5 and $C_{max}$ of losartan reduces by about 10% after food absorption, it needs an effort to develop a formulation which can exhibit a high losartan dissolution rate over the normal pH range in the stomach, i.e., pH 1.0 to 3.5.

The present inventors have found that the dissolution rates of amlodipine and losartan greatly depend on the used amount of losartan, especially, at a low pH. Therefore, the present invention also includes within its scope a solid pharmaceutical composition with the specific amount of losartan which exhibits optimized dissolution rates of amlodipine and losartan.

Figure 2:
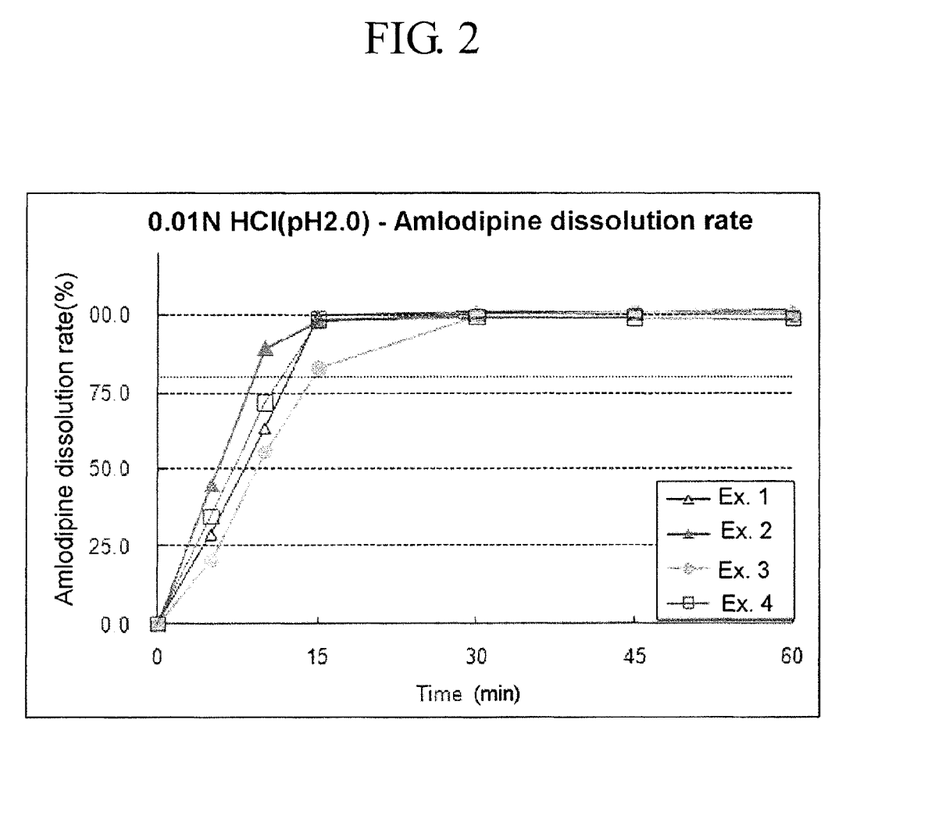
FIG. 2: amlodipine dissolution rates in 0.01N HCl (pH 2.0) observed for the tablets prepared in Examples 1 to 4 (Test Example 2)

The inventive composition comprising amlodipine and losartan which exhibits high dissolution rates of amlodipine and losartan at the pH value ranging from 1.0 to 2.0, which belongs to that in the stomach of a normal adult, contain losartan in an amount ranging, preferably, from 3 to 25% by weight, more preferably, from 5 to 22.3% by weight based on the total weight of the composition. When the amount of losartan is 25% by weight or less, both of dissolution rates at a low pH of amlodipine and losartan become increased. Specifically, amlodipine in the combined formulation containing losartan in an amount of 25% by weight or less is very well released even under a low pH condition and, in particular, such a formulation can meet the dissolution criteria of amlodipine, i.e., 80% or more thereof in 30 minutes at pH 1.0-2.0 (see FIGS. 2 to 4). In addition, the combined formulation containing losartan in an amount of 25% by weight or less exhibits a significantly high losartan dissolution rate under a low pH condition as compared to Cozaar (trade mark) tablet, the conventional single losartan formulation (see FIG. 5). Accordingly, it is expected that the inventive combined formulation can show markedly high bioavailabilities of amlodipine and losartan. Meanwhile, when the amount of losartan is below 3% by weight, the overall size of the formulation is too big, which deteriorates the patient compliance.

In accordance with another embodiment of the present invention, the present invention also includes within its scope a solid pharmaceutical composition which comprises granule forms of amlodipine and losartan separated from each other, and contains losartan in an amount ranging from 3 to 25% by weight based on the total weight of the composition. Further, the present invention provides a solid pharmaceutical composition comprising a granule form of losartan of which the percentage of a fine granule passing through a 75 mesh is below 50%, preferably below 25%, more preferably below 10%.

In this regard, the present inventors have found that, besides the overall used amount of losartan, the dissolution rates of amlodipine and losartan significantly depend on the particle size of losartan granules, especially, at a low pH. More specifically, they have found that lowering of the partial ratio of fine granules in the losartan granules results in improvement of the amlodipine and losartan dissolution rates.

Therefore, in accordance with still another embodiment of the present invention, the present invention also includes within its scope a solid pharmaceutical composition which comprises granule forms of amlodipine and losartan separated from each other, wherein, in a losartan granule part, the percentage of a fine granule passing through a 75 μm is below 50%.

The inventive composition may further comprise a stabilizing agent such as an anti-oxidant which functions to enhance stability of amlodipine against the undesired reaction with other pharmaceutically acceptable excipients during a blending process, and against deformation of amlodipine by light or moisture with the passage of time. Representative examples of the anti-oxidant used in the present invention include butylated hydroxytoluene (BHT), butylated hydroxyanisole (BHA), ascorbic acid, ascorbyl palmitic acid, ethylene diamine tetracetic acid (EDTA), sodium pyrosulfite and a mixture thereof. Among the above anti-oxidants, butylated hydroxytoluene is most preferred in the present invention.

In accordance with yet another embodiment of the present invention, the present invention also includes within its scope a method for preparing a solid pharmaceutical composition comprising granule forms of amlodipine and losartan separated from each other, which comprises the steps of:

a) granulating and drying a mixture of losartan or a pharmaceutically acceptable salt thereof and a pharmaceutically acceptable excipient to obtain losartan granules;

b) granulating and drying a mixture of amlodipine or a pharmaceutically acceptable salt thereof and a pharmaceutically acceptable excipient to obtain amlodipine granules; and c) mixing the losartan granules obtained in step a) with the amlodipine granules obtained in step b).

In the granulation process of step a) or b), conventional wet-granulation or dry-granulation techniques may be used.

The composition of the present invention may be administered in the form of a tablet, a capsule or multi-particles through various routes of oral administration including oral cavity, mouth and hypoglossus. However, it is understood that the administration route of the inventive composition should be determined by the doctor in charge based on the patient's symptoms and requirements.

The inventive composition may be preferably formulated into the tablet form. Preferably, such a tablet obtained from the inventive composition may have an outer coating layer, and the coating layer may consist of any one of conventional high molecular compounds which are capable of forming the film coating. The amount of the coating should be reduced to a minimum for easy administration and manufacturing efficiency, and it may be in a range of about 1 to 10% by weight, preferably about 3 to 5% by weight, based on the total weight of the formulation. This coating may be performed in accordance with any one of conventional tablet coating methods. The tablet having the above composition, prepared by the above method is very stable under a conventional storage condition, and against light and moisture.

The following Examples are intended to further illustrate the present invention without limiting its scope.

Example 1

Preparation of Combined Tablet—(I)

| Losartan granule part - | |
|---|---|
| losartan potassium | 50.0 mg |
| microcrystalline cellulose | 175.0 mg |
| crosspovidone | 12.0 mg |
| Amlodipine granule part - | |
| amlodipine camsylate | 7.84 mg (amlodipine 5 mg) |
| butylated hydroxytoluene | 0.1 mg |
| microcrystalline cellulose | 90.0 mg |
| mannitol | 40.0 mg |
| sodium starch glycolate | 17.0 mg |
| polyvinylpyrrolidone | 5.0 mg |
| purified water | (65.0 mg) |
| Lubricants - | |
| magnesium stearate | 3.0 mg |
| Coating part - | |
| hypromellose | 8.0 mg |
| hydroxypropyl cellulose | 2.0 mg |
| titanium dioxide | 2.0 mg |
| talc | 0.1 mg |
| ethanol | (200.0 mg) |
| purified water | (50.0 mg) |

The ingredients of the losartan granule part were dry-granulated using a roller compactor to prepare the losartan granule part having fine granules which passed through a 75 μm mesh in an amount of 20% by weight or less. The ingredients of the amlodipine granule part were wet-granulated using 65.0 mg/tablet of purified water, passed through a mesh, and dried to prepare the amlodipine granule part having the specified amounts of the ingredients. The amlodipine granule part was mixed with the losartan granule part using a mixer for 30 minutes. Subsequently, a magnesium stearate lubricant was added thereto according to the corresponding amounts, and mixed for 5 minutes. The resulting mixture was formulated into a tablet and the formulated tablet was coated using a coating composition having the specified amounts of the ingredients of the coating part to obtain a combined tablet. The combined tablet contains 5 mg of amlodipine and 50 mg of losartan, wherein the losartan amount corresponds to about 12.5% of the weight of the tablet except for the coating part.

Example 2

Preparation of Combined Tablet—(II)

| Losartan granule part - | |
|---|---|
| losartan potassium | 50.0 mg |
| calcium dihydrogen phosphate | 175.0 mg |
| crosspovidone | 12.0 mg |
| Amlodipine granule part - | |
| amlodipine camsylate | 7.84 mg (amlodipine 5 mg) |
| butylated hydroxytoluene | 0.1 mg |
| calcium dihydrogen phosphate | 90.0 mg |
| mannitol | 40.0 mg |
| sodium starch glycolate | 17.0 mg |
| polyvinylpyrrolidone | 5.0 mg |
| purified water | (65.0 mg) |
| Lubricants - | |
| magnesium stearate | 3.0 mg |

A combined tablet was prepared by repeating the procedure of Example 1 except for using calcium dihydrogen phosphate instead of microcrystalline cellulose in each of the losartan and amlodipine granule parts. The combined tablet contains 5 mg of amlodipine and 50 mg of losartan, wherein the losartan amount corresponds to about 12.5% of the weight of the tablet except for the coating part.

Example 3

Preparation of Combined Tablet—(III)

| Losartan granule part - | |
|---|---|
| losartan potassium | 50.0 mg |
| microcrystalline cellulose | 175.0 mg |
| crosspovidone | 12.0 mg |
| Amlodipine granule part - | |
| amlodipine camsylate | 15.68 mg (amlodipine 10 mg) |
| butylated hydroxytoluene | 0.2 mg |
| microcrystalline cellulose | 90.0 mg |
| mannitol | 40.0 mg |
| sodium starch glycolate | 17.0 mg |
| polyvinylpyrrolidone | 5.0 mg |
| purified water | (65.0 mg) |
| Lubricants - | |
| magnesium stearate | 3.0 mg |
| Coating part - | |
| hypromellose | 8.0 mg |
| hydroxypropyl cellulose | 2.0 mg |
| titanium dioxide | 2.0 mg |
| talc | 0.1 mg |
| ethanol | (200.0 mg) |
| purified water | (50.0 mg) |

A combined tablet was prepared by repeating the procedure of Example 1 except for using twice amounts of each of amlodipine and butylated hydroxytoluene. The combined tablet contains 10 mg of amlodipine and 50 mg of losartan, wherein the losartan amount corresponds to about 12.3% of the weight of the tablet except for the coating part.

Example 4

Preparation of Combined Tablet—(IV)

| Losartan granule part - | |
|---|---|
| losartan potassium | 100.0 mg |
| microcrystalline cellulose | 350.0 mg |
| crosspovidone | 24.0 mg |
| Amlodipine granule part - | |
| amlodipine camsylate | 15.68 mg (amlodipine 10 mg) |
| butylated hydroxytoluene | 0.2 mg |
| microcrystalline cellulose | 90.0 mg |
| mannitol | 40.0 mg |
| sodium starch glycolate | 17.0 mg |
| polyvinylpyrrolidone | 5.0 mg |
| purified water | (65.0 mg) |
| Lubricants - | |
| magnesium stearate | 5.0 mg |
| Coating part - | |
| hypromellose | 8.0 mg |
| hydroxypropyl cellulose | 2.0 mg |
| titanium dioxide | 2.0 mg |
| talc | 0.1 mg |
| ethanol | (200.0 mg) |
| purified water | (50.0 mg) |

A combined tablet was prepared by repeating the procedure of Example 3 except for using twice amounts of each of the ingredients of the losartan granule part and 5 mg of magnesium stearate. The combined tablet contains 10 mg of amlodipine and 100 mg of losartan, wherein the losartan amount corresponds to about 15.5% of the weight of the tablet except for the coating part.

Example 5

Preparation of Combined Tablet—(V)

| Losartan granule part - | |
|---|---|
| losartan potassium | 50.0 mg |
| microcrystalline cellulose | 25.0 mg |
| crosspovidone | 12.0 mg |
| Amlodipine granule part - | |
| amlodipine camsylate | 7.84 mg (amlodipine 5 mg) |
| butylated hydroxytoluene | 0.1 mg |
| microcrystalline cellulose | 90.0 mg |
| mannitol | 40.0 mg |
| sodium starch glycolate | 17.0 mg |
| polyvinylpyrrolidone | 5.0 mg |
| purified water | (65.0 mg) |
| Lubricants - | |
| magnesium stearate | 3.0 mg |
| Coating part - | |
| hypromellose | 8.0 mg |
| hydroxypropyl cellulose | 2.0 mg |
| titanium dioxide | 2.0 mg |
| talc | 0.1 mg |
| ethanol | (200.0 mg) |
| purified water | (50.0 mg) |

A combined tablet comprising losartan in an amount of about 20% of the weight of the tablet except for the coating part was prepared by repeating the procedure of Example 1 except for using the ingredients in specified amounts as described above.

Example 6

Preparation of Combined Tablet—(VI)

| Losartan granule part - | |
|---|---|
| losartan potassium | 50.0 mg |
| microcrystalline cellulose | 350.0 mg |
| crosspovidone | 24.0 mg |
| Amlodipine granule part - | |
| amlodipine camsylate | 7.84 mg (amlodipine 5 mg) |
| butylated hydroxytoluene | 0.1 mg |
| microcrystalline cellulose | 90.0 mg |
| mannitol | 40.0 mg |
| sodium starch glycolate | 17.0 mg |
| polyvinylpyrrolidone | 5.0 mg |
| purified water | (65.0 mg) |
| Lubricants - | |
| magnesium stearate | 5.0 mg |
| Coating part - | |
| hypromellose | 8.0 mg |
| hydroxypropyl cellulose | 2.0 mg |
| titanium dioxide | 2.0 mg |
| talc | 0.1 mg |
| ethanol | (200.0 mg) |
| purified water | (50.0 mg) |

A combined tablet comprising losartan in an amount of about 8.5% of the weight of the tablet except for the coating part was prepared by repeating the procedure of Example 1 except for using the ingredients in specified amounts as described above.

Example 7

Preparation of Combined Tablet—(Vii)

| Losartan granule part - | |
|---|---|
| losartan potassium | 50.0 mg |
| crosspovidone | 12.0 mg |
| Amlodipine granule part - | |
| amlodipine camsylate | 7.84 mg (amlodipine 5 mg) |
| butylated hydroxytoluene | 0.1 mg |
| microcrystalline cellulose | 90.0 mg |
| mannitol | 40.0 mg |
| sodium starch glycolate | 17.0 mg |
| polyvinylpyrrolidone | 5.0 mg |
| purified water | (65.0 mg) |
| Lubricants - | |
| magnesium stearate | 3.0 mg |
| Coating part - | |
| hypromellose | 8.0 mg |
| hydroxypropyl cellulose | 2.0 mg |
| titanium dioxide | 2.0 mg |
| talc | 0.1 mg |
| ethanol | (200.0 mg) |
| purified water | (50.0 mg) |

A combined tablet comprising losartan in an amount of about 22.2% of the weight of the tablet except for the coating part was prepared by repeating the procedure of Example 1 except for using the ingredients in specified amounts as described above.

Comparative Example 1

Preparation of Direct-Compression Tablet Comprising a Simple Mixture of Amlodipine and Losartan

| Mixing part - | |
|---|---|
| amlodipine camsylate | 7.84 mg (amlodipine 5 mg) |
| losartan potassium | 50.0 mg |
| microcrystalline cellulose | 150.0 mg |
| calcium dihydrogen phosphate | 60.0 mg |
| sodium starch glycolate | 24.0 mg |
| polyvinylpyrrolidone | 3.0 mg |
| Lubricants - | |
| magnesium stearate | 2.0 mg |

All ingredients were mixed together according to the corresponding amounts, and the resulting mixture was formulated into a direct-compression tablet. The direct-compression tablet contains 5 mg of amlodipine and 50 mg of losartan, wherein the losartan amount corresponds to about 16.8% of the weight of the tablet.

Comparative Example 2

Preparation of Combined Tablet—(VIII)

| Losartan granule part - | |
|---|---|
| losartan potassium | 100.0 mg |
| microcrystalline cellulose | 38.0 mg |
| crosspovidone | 12.0 mg |
| Amlodipine granule part - | |
| amlodipine camsylate | 7.84 mg (amlodipine 5 mg) |
| butylated hydroxytoluene | 0.1 mg |
| microcrystalline cellulose | 90.0 mg |
| mannitol | 40.0 mg |
| sodium starch glycolate | 17.0 mg |
| polyvinylpyrrolidone | 5.0 mg |
| purified water | (65.0 mg) |
| Lubricants - | |
| magnesium stearate | 3.0 mg |
| Coating part - | |
| hypromellose | 8.0 mg |
| hydroxypropyl cellulose | 2.0 mg |
| titanium dioxide | 2.0 mg |
| talc | 0.1 mg |
| ethanol | (200.0 mg) |
| purified water | (50.0 mg) |

A combined tablet comprising losartan in an amount of about 32.0% of the weight of the tablet except for the coating part was prepared by repeating the procedure of Example 1 except for using the ingredients in specified amounts as described above.

Hereinafter, the properties of formulations according to Example 1 to 7 and Comparative Example 1 and 2 are shown in Table 1.

TABLE 1

| | Weight of formulation (mg) | Amount of losartan (mg) | Weight Percentage of losartan (%) | Formulation type |
|---|---|---|---|---|
| Example 1 | 400 | 50 | 12.5 | Tablet comprising the separated granules of losartan and amlodipine (coated) |
| Example 2 | 400 | 50 | 12.5 | Tablet comprising the separated granules of losartan and amlodipine (non-coated) |
| Example 3 | 408 | 50 | 12.3 | Tablet comprising the separated granules of losartan and amlodipine (coated) |
| Example 4 | 647 | 100 | 15.5 | Tablet comprising the separated granules of losartan and amlodipine (coated) |
| Example 5 | 250 | 50 | 20.0 | Tablet comprising the separated granules of losartan and amlodipine (coated) |
| Example 6 | 589 | 50 | 8.5 | Tablet comprising the separated granules of losartan and amlodipine (coated) |
| Example 7 | 225 | 50 | 22.2 | Tablet comprising the separated granules of losartan and amlodipine (coated) |
| Comparative Example 1 | 297 | 50 | 16.8 | Tablet comprising the mixture of losartan and amlodipine (non-coated) |
| Comparative Example 2 | 313 | 100 | 32.0 | Tablet comprising the separated granules of losartan and amlodipine (coated) |

Test Example 1

Dissolution Test of Amlodipine

Figure 1:
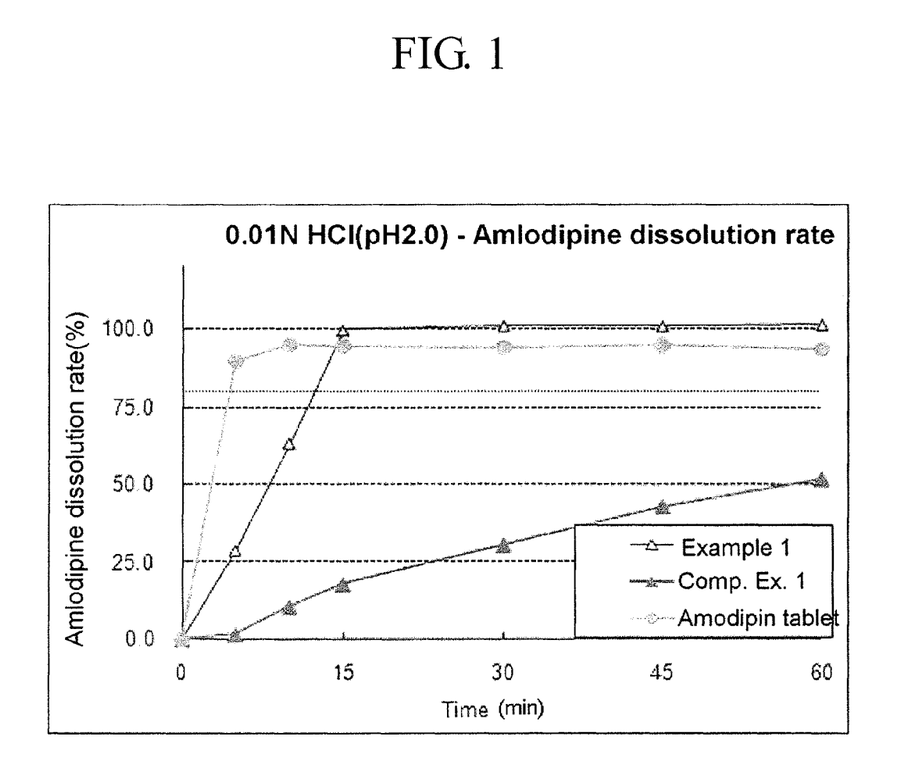
FIG. 1: amlodipine dissolution rates in 0.01N HCl (pH 2.0) observed for the tablets prepared in Example 1 and Comparative Example 1, and Amodipin (trade mark) tablet (Test Example 1)

The combined tablet containing 5 mg of amlodipine and 50 mg of losartan obtained in Example 1, the direct-compression tablet comprising the mixture of losartan and amlodipine obtained in Comparative Example 1, and Amodipin (trade mark) as an amlodipine camsylate formulation, were each subjected to a drug dissolution test under the following conditions.
—Test Conditions—
Effluent: 500 ml of 0.01N HCl (pH 2.0)
Dissolution-test system: USP paddle method, 75 rpm
Temperature: 37° C.
—Analytical Conditions—
Column: stainless steel column (inner diameter: 4.6 mm, length: 15 cm) filled with octadecylsilanized silica gel for 5 μm liquid chromatography
Mobile phase: a mixture of methonol and 0.03M potassium dihydrogen phosphate (600:400, v/v)
Detector: ultraviolet spectrophotometer (350 nm)
Flow rate: 1.5 ml/min
Injection volume: 20 μl
—Criteria of Dissolution Rate—
more than 80% at 30 minutes
—Results—
As shown in FIG. 1, the combined tablet prepared by using the separated granules of amlodipine and losartan according to Example 1 exhibited an amlodipine dissolution rate higher by twice or more than that of the direct-compression tablet obtained in Comparative Example 1. Further, the dissolution rate of the tablet prepared in Comparative Example 1 did not satisfy the required criteria, while that of the tablet of Example 1 met the criteria.

Test Example 2

Dissolution Test of Amlodipine for the Formulations of Examples 1 to 4

Figure 3:
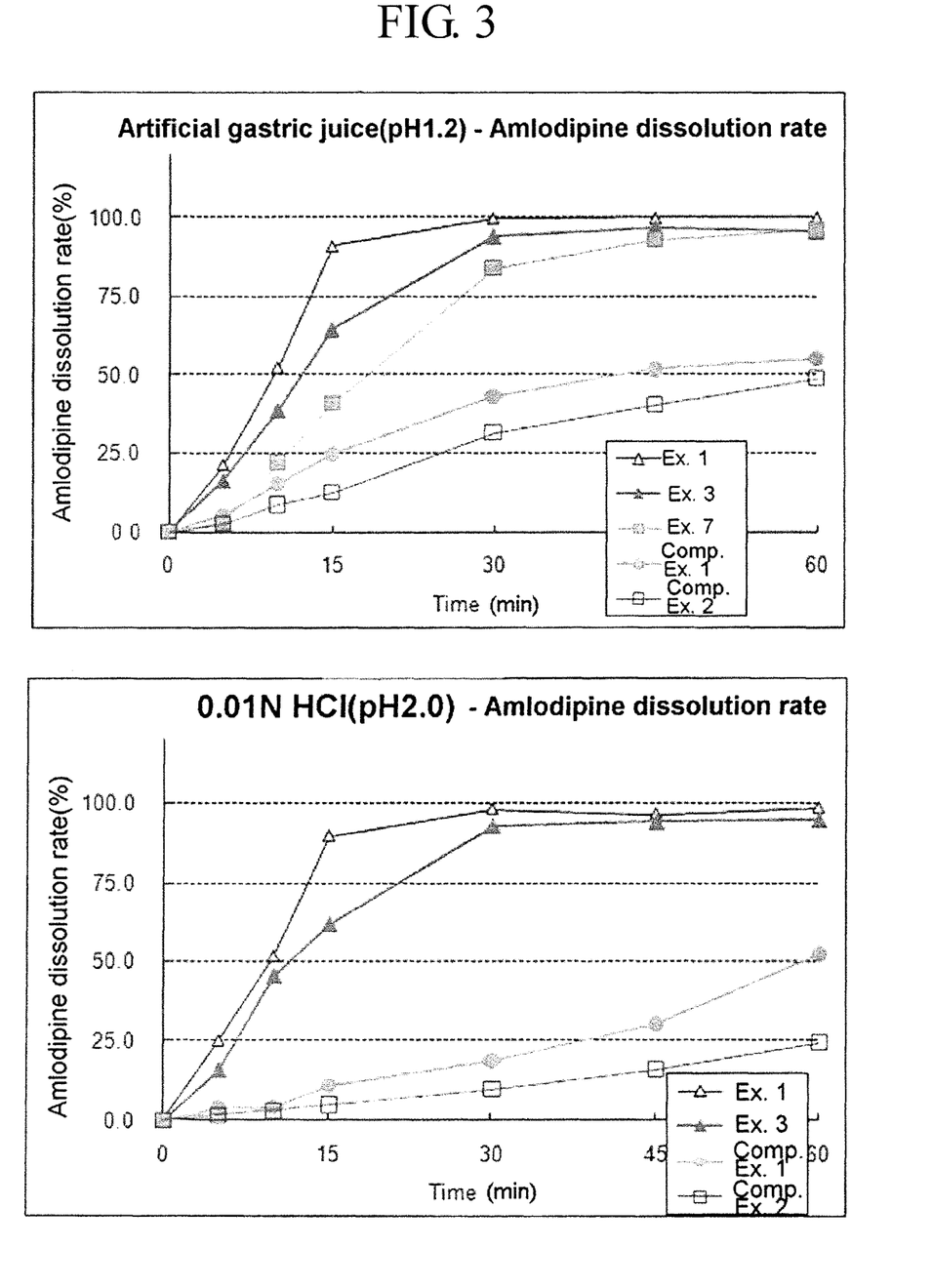
FIG. 3: amlodipine dissolution rates in artificial gastric juice (pH 1.2) as well as in 0.01N HCl (pH 2.0) observed for the tablets prepared in Examples 1, 3 and 7, and Comparative Examples 1 and 2 (Test Example 3)

The combined tablets of Examples 1 to 4 were each subjected to drug dissolution test under the same test and analytical conditions of Test Example 1.
—Results—
As can be seen in FIG. 3, the combined tablets obtained in Examples 2 to 4 exhibited high and stable amlodipine dissolution rates, similar to that of the tablet of Example 1 at 0.01N HCl (pH 2.0). From the result, it is confirmed that the combined tablets exhibit high and stable amlodipine dissolution rates regardless of the kind of the excipient, and the amount of amlodipine or the losartan granule part, only if the weight percentage of losartan in the combined tablet does not go beyond an appropriate level.

Test Example 3

Dissolution Test of Amlodipine for the Formulations of Examples 1, 3 and 7, and Comparative Examples 1 and 2

The tablets prepared in Examples 1, 3 and 7, and Comparative Examples 1 and 2 were each subjected to a drug dissolution test under the same test and analytical conditions of Test Example 1.
—Test Conditions—
Effluent: 900 ml of artificial gastric juice (pH 1.2) or 0.01N HCl (pH 2.0)
Dissolution-test system: USP paddle method, 50 rpm
Temperature: 37° C.
—Results—
The above dissolution-test system (USP paddle method, 50 rpm) is the most widely used to evaluate a dissolution rate of drug for the oral formulations, and the used effluent (the artificial gastric juice (pH 1.2) or 0.01N HCl (pH 2.0)) has pH similar to that of the gastrointestinal tract.
As shown in FIG. 3, the combined tablets obtained in Examples 1, 3 and 7 exhibited even higher amlodipine dissolution rates than those of the tablets obtained in Comparative Examples 1 and 2. The result suggests that the dissolution rate at 30 min of the formulation, which contains separated granules of losartan and amlodipine and comprises losartan in an amount of 25% by weight or less, was 80% or more at low pH (pH 1.2 and pH 2), which meets the criteria.

Test Example 4

Dissolution Test of Amlodipine for the Formulations of Examples 4 to 6 and Comparative Example 2

The combined tablets obtained in Example 4 to 6 and Comparative Example 2 were each subjected to a drug dissolution test under the same test and analytical conditions of Test Example 1.

—Results—

Figure 4:
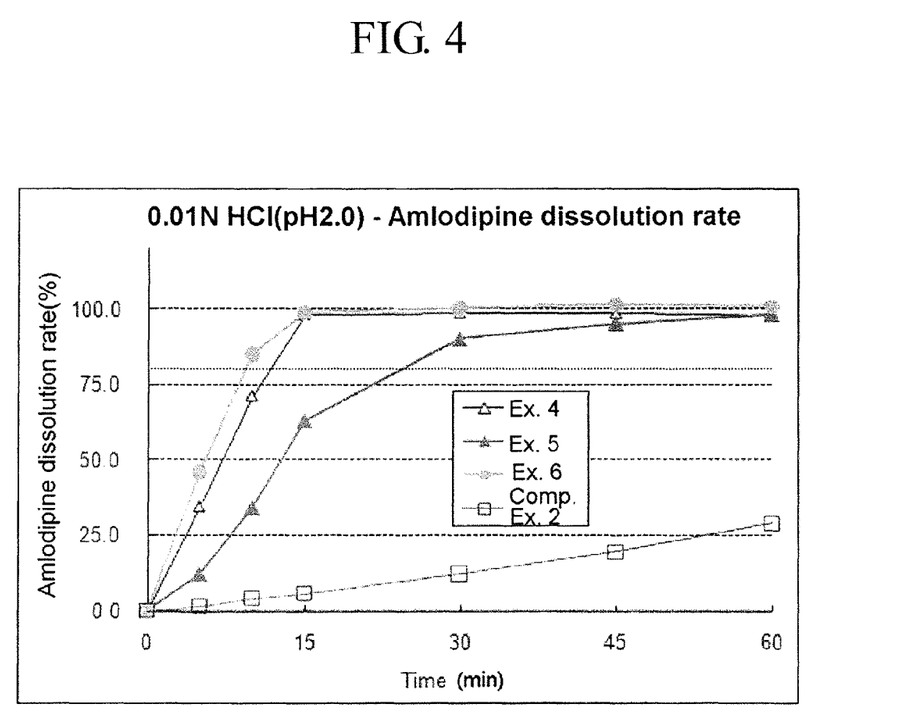
FIG. 4: amlodipine dissolution rates in 0.01N HCl (pH 2.0) observed for the tablets prepared in Examples 4 to 6 and Comparative Example 2 (Test Example 4)

As shown in FIG. 4, the dissolution rates at 30 minutes of the combined tablets obtained in Example 4 to 6 were 80% or more, which was identical to the result in Test Example 3.

Test Example 5

Dissolution Test of Losartan for the Formulations of Examples 1, 3 and 7, and Comparative Examples 1 and 2

The tablets obtained in Examples 1, 3 and 7, Comparative Examples 1 and 2, and Cozaar (trade mark) were each subjected to a drug dissolution test under the following conditions.

—Test Conditions—
Effluent: 900 ml of artificial gastric juice (pH 1.2) or 0.01N HCl (pH 2.0)
Dissolution-test system: USP paddle method, 50 rpm
Temperature: 37° C.
—Analytical Conditions—
Column: stainless steel column (inner diameter: 4.6 mm, length: 15 cm) filled with octadecylsilanized silica gel for 5 μm liquid chromatography
Mobile phase:
  mobile phase A—phosphate buffer:acetonitrile (850:150, v/v)
  mobile phase B—acetonitrile
  concentration gradient system

| Time (min) | Mobile phase A % | Mobile phase B % |
|---|---|---|
| 0 | 80 | 20 |
| 10 | 40 | 60 |
| 11 | 80 | 20 |
| 15 | 80 | 20 |

Detector: ultraviolet spectrophotometer (250 nm)
Flow rate: 1.5 ml/min
Injection volume: 10 μl
—Results—
The above dissolution-test system (USP paddle method, 50 rpm) is the most widely used to evaluate a dissolution rate of drug for the oral formulations, and the used effluent (the artificial gastric juice (pH 1.2) or 0.01N HCl (pH 2.0)) has pH similar to that of the gastrointestinal tract.

Figure 5:
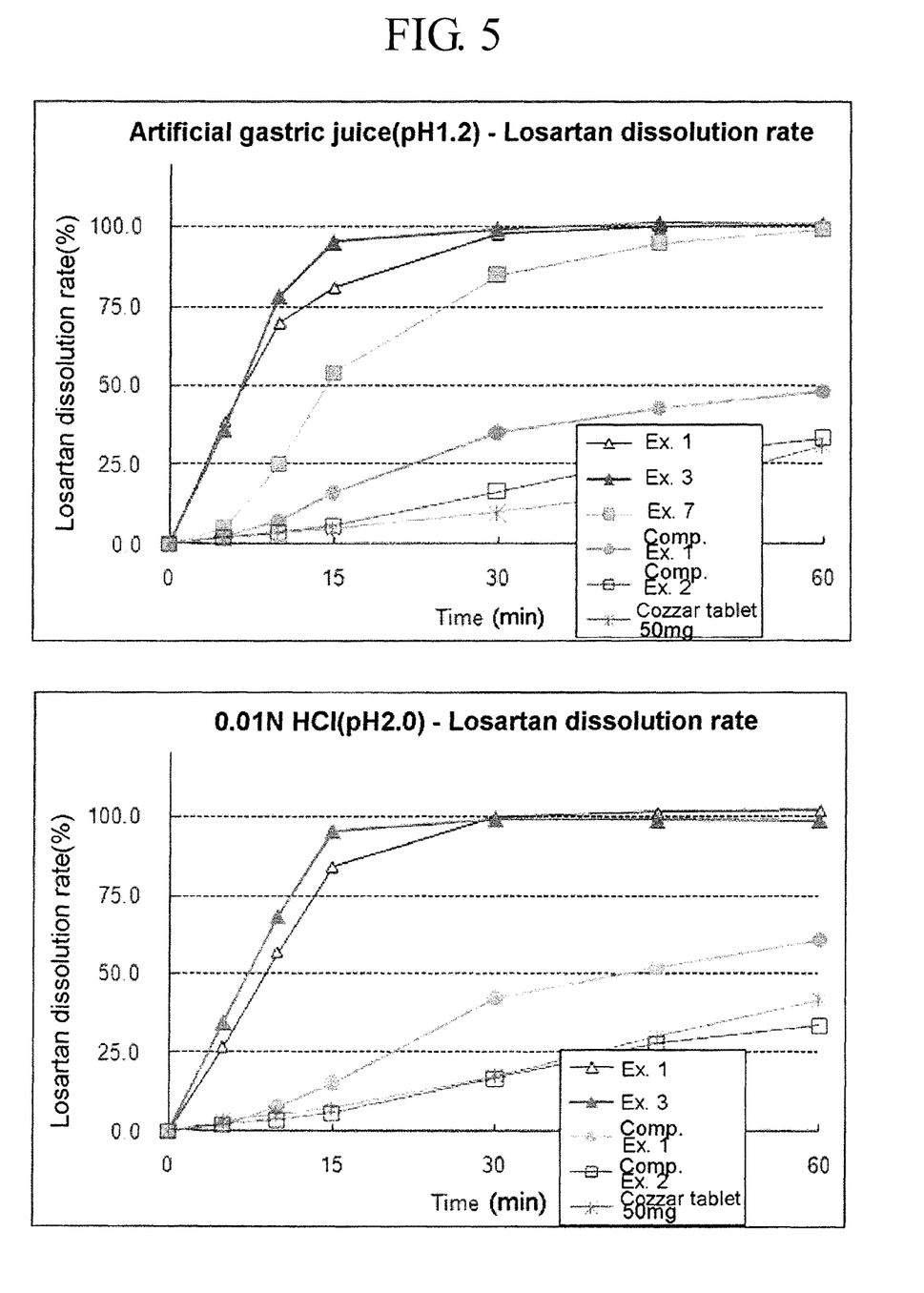
FIG. 5: losartan dissolution rates in artificial gastric juice (pH 1.2) as well as in 0.01N HCl (pH 2.0) observed for the tablets prepared in Examples 1, 3 and 7, Comparative Examples 1 and 2, and Cozaar (trade mark) tablet (Test Example 5).

As shown in FIG. 5, the combined tablets obtained in Examples 1, 3 and 7 exhibited even higher losartan dissolution rates than those of the tablets obtained in Comparative Examples 1 and 2, and Cozaar (trade mark) which is a single formulation of losartan.

Test Example 6

Stability Test of Amlodipine

A stability test was performed for the combined tablet obtained in Example 1, which was prepared by using the separated granules of amlodipine and losartan, and the direct-compression tablet obtained in Comparative Example 1 under the following conditions.
Incubation conditions: HDPE bottle at 40° C./75% relative humidity
Incubation time: 0, 1, 2, 4 and 6 months
Subject of test: amlodipine
Analytical conditions: the analytical conditions of Example 1

The results are shown in Table 2.

TABLE 2

| Formulation | 0 | 1 month | 2 months | 4 months | 6 months |
|---|---|---|---|---|---|
| Example 1 | 100.0% | 99.9% | 99.6% | 99.8% | 99.5% |
| Comparative Example 1 | 100.2% | 97.8% | 94.9% | 90.3% | 85.7% |

As shown in Table 2, the combined tablet obtained in Example 1 exhibited a higher amlodipine stability as compared with the direct-compression tablet obtained in Comparative Example 1.

While the invention has been described with respect to the above specific embodiments, it should be recognized that various modifications and changes may be made to the invention by those skilled in the art which also fall within the scope of the invention as defined by the appended claims.

What is claimed is:

1. A solid pharmaceutical composition comprising amlodipine or a pharmaceutically acceptable salt thereof and losartan or a pharmaceutically acceptable salt thereof,
wherein amlodipine or a pharmaceutically acceptable salt thereof is of granular form, and losartan or a pharmaceutically acceptable salt thereof is of granule form, wherein the granule of amlodipine or a pharmaceutically acceptable salt thereof and the granule of losartan or a pharmaceutically acceptable salt thereof are separated from each other;
wherein the composition comprises losartan or a pharmaceutically acceptable salt thereof in an amount ranging from 5 to 22.3% by weight based on the total weight of the composition;
wherein the composition comprises a granule form of losartan of which the percentage of a fine granule passing through a 75 μm mesh is below 50%;
wherein the dissolution rate of amlodipine in the solid pharmaceutical composition is 80% or more thereof in 30 minutes at a pH range of 1.0 to 2.0; and
wherein the dissolution rate of losartan in the solid pharmaceutical composition is 80% or more thereof in 30 minutes at a pH range of 1.0 to 2.0.

2. The composition of claim 1, which comprises a granule form of losartan of which the percentage of a fine granule passing through a 75 μm mesh is below 25%.

3. The composition of claim 2, which comprises a granule form of losartan of which the percentage of a fine granule passing through a 75 μm mesh is below 10%.

4. The composition of claim 1, wherein the pharmaceutically acceptable salt of amlodipine is amlodipine camsylate.

5. A method for preparing the solid composition of claim 1 comprising amlodipine in a granule form and losartan in a granule form, said amlodipine granules and losartan granules being separated from each other, which comprises the steps of:
a) granulating and drying a mixture of losartan or a pharmaceutically acceptable salt thereof and a pharmaceutically acceptable excipient to obtain losartan granules;
b) granulating and drying a mixture of amlodipine or a pharmaceutically acceptable salt thereof and a pharmaceutically acceptable excipient to obtain amlodipine granules; and
c) mixing the losartan granules obtained in step a) with the amlodipine granules obtained in step b) to give the composition, wherein the solid composition comprises losartan or a pharmaceutically acceptable salt thereof in an amount ranging from 5 to 22.3% by weight based on the total weight of the composition;

wherein the composition comprises a granule form of losartan of which the percentage of a fine granule passing through a 75 μm mesh is below 50%;

wherein the dissolution rate of amlodipine in the solid pharmaceutical composition is 80% or more thereof in 30 minutes at a pH range of 1.0 to 2.0; and wherein the dissolution rate of losartan in the solid pharmaceutical composition is 80% or more thereof in 30 minutes at a pH range of 1.0 to 2.0.

* * * * *